United States Patent [19]

Muramatsu et al.

[11] 4,351,954

[45] Sep. 28, 1982

[54] HALOGENATED α-AMINO ACIDS

[75] Inventors: Hiroshige Muramatsu; Teruo Ueda, both of Nagoya, Japan

[73] Assignees: Agency of Industrial Science & Technology; Ministry of International Trade & Industry, both of Tokyo, Japan

[21] Appl. No.: 289,183

[22] Filed: Aug. 3, 1981

Related U.S. Application Data

[63] Continuation-in-part of Ser. No. 192,808, Oct. 1, 1980, abandoned.

[30] Foreign Application Priority Data

Oct. 13, 1979 [JP] Japan .............................. 54-132017

[51] Int. Cl.³ .......................................... C07C 101/10
[52] U.S. Cl. ...................................... 562/574; 71/113; 424/319; 204/163 R; 560/227; 560/172; 260/349

[58] Field of Search ........................................ 562/574

[56] References Cited

FOREIGN PATENT DOCUMENTS 2742686 4/1979 Fed. Rep. of Germany ...... 560/172

OTHER PUBLICATIONS

Brace, J. Org. Chem., 32, p. 430–434, (1967).
Maki, Yuki Gosei Kagaku Shi, 34, pp. 722–725, (1976).

*Primary Examiner*—Michael L. Shippen
*Attorney, Agent, or Firm*—Kurt Kelman

[57] ABSTRACT

Halogenated α-amino acids as new compounds are obtained by subjecting halogenated ethanes and an ester of acrylic acid or crotonic acid to addition reaction, adding sodium azide to the adducts, reducing the resultant mixtures with hydrogen and subsequently hydrolyzing the reduction products.

1 Claim, No Drawings

HALOGENATED α-AMINO ACIDS

REFERENCE OF COPENDING APPLICATION

This application is a continuation-in-part of our copending application Ser. No. 192,808, filed Oct. 1, 1980, now abandoned.

BACKGROUND OF THE INVENTION

This invention relates to novel halogenated α-amino acids demonstrating an ability to eradicate harmful insects, fungi and weeds and inhibit acid phosphatase and other enzymes and to a method for the manufacture of such halogenated α-amino acids.

Heretofore, α-amino acids possessing a perfluoroalkyl ($C_2F_{2n+1}$) group have been known to the art [as reported in Journal of Organic Chemistry, Vol. 32, page 430 (1967), for example]. However, the α-amino acids of this invention which simultaneously contain fluorine and chlorine or bromine have never been known to the art.

SUMMARY OF THE INVENTION

One object of this invention is to provide novel halogenated α-amino acids which posses an ability to eradicate harmful insects, fungi and weeds and inhibit acid phosphatase and other enzymes.

Another object of this invention is to provide a method for the manufacture of the novel halogenated α-amino acids mentioned above.

The first object of this invention is accomplished by preparation of halogenated α-amino acids represented by the general formula:

$$\underset{\underset{R}{|}\phantom{CHCHCO_2H}\underset{NH_2}{|}}{CF_2XCFX'CHCHCO_2H}$$

(wherein, X stands for Cl or Br, X' for F, Cl or H, and R for H or CH$_3$), which are novel compounds not yet reported in the literature.

The second object of this invention is accomplished by subjecting a halogenated ethane of the general formula:

$$CF_2XCFX'I$$

(wherein, X stands for Cl or Br, and X' for F, Cl or H) and a (methyl or ethyl) ester of acrylic acid or crotonic acid to addition reaction under the radition of light thereby producing an adduct represented by the general formula:

$$\underset{\underset{R}{|}\phantom{CHCHCO_2R'}\underset{I}{|}}{CF_2XCFX'CHCHCO_2R'}$$

(wherein, X and X' have the same meanings as described above, R stands for H or CH$_3$, and R' for CH$_3$ or C$_2$H$_5$), causing this adduct to react with sodium azide thereby producing an azide compound represented by the general formula:

$$\underset{\underset{R}{|}\phantom{CHCHCO_2R'}\underset{N_3}{|}}{CF_2XCFX'CHCHCO_2R'}$$

(wherein, X, X', R and R' have the same meanings as described above), subsequently reducing the azide compound with hydrogen thereby producing an α-amino ester represented by the general formula:

$$\underset{\underset{R}{|}\phantom{CHCHCO_2R'}\underset{NH_2}{|}}{CF_2XCFX'CHCHCO_2R'}$$

(wherein, X, X', R and R' have the same meanings as described above) and hydrolyzing the α-amino ester in the presence of an inorganic acid such as sulfuric acid or hydrochloric acid thereby producing a halogenated α-amino acid represented by the general formula:

$$\underset{\underset{R}{|}\phantom{CHCHCO_2H}\underset{NH_2}{|}}{CF_2XCFX'CHCHCO_2H}$$

(wherein, X, X' and R have the same meanings as described above).

DETAILED DESCRIPTION OF THE INVENTION

The halogenated α-amino acids of the present invention are represented by the general formula:

$$\underset{\underset{R}{|}\phantom{CHCHCO_2H}\underset{NH_2}{|}}{CF_2XCFX'CHCHCO_2H}$$

(wherein, X stands for Cl or Br, X' for F, Cl or H, and R for H or CH$_3$). The compounds of the present invention not only demonstrate bioactivity but may convert through such reactions as substitution, dehalogenation and reduction into other useful fluorine-containing amino acids because of their inclusion of reactive halogen atoms such as chlorine or bromine atoms.

The compounds of this invention are easily produced by subjecting halogenated ethanes represented by the general formula:

$$CF_2XCFX'I$$

(wherein, X stands for Cl or Br, and X' for F, Cl or H) and a (methyl or ethyl) ester of acrylic acid or crotonic acid to addition reaction under the radiation of light, causing the resultant adducts $$\underset{\underset{R}{|}\phantom{CHCHCO_2R')}\underset{I}{|}}{(CF_2XCFX'CHCHCO_2R')}$$

to react with sodium azide thereby producing azide compounds $$\underset{\underset{R}{|}\phantom{CHCHCO_2R'),}\underset{N_3}{|}}{(CF_2XCFX'CHCHCO_2R'),}$$

subsequently reducing the azide compounds with hydrogen into α-amino esters $$\underset{\underset{R}{|}\phantom{CHCHCO_2R')}\underset{NH_2}{|}}{(CF_2XCFX'CHCHCO_2R')}$$

and finally hydrolyzing the α-amino esters in the presence of an inorganic acid such as sulfuric acid or hydrochloric acid. The halogenated ethanes (CF$_2$XCFX'I) to be used as the starting material for the compounds of the present invention are easily prepared by the addition reaction of fluoroethylene and an interhalogen compound.

Now, the physical and chemical properties of the halogenated α-amino acids which are novel compounds of this invention and the identification of the compounds will be described below.

The halogenated α-amino acids are white plate-shaped crystals which melt and decompose at temperatures within the range of from 170° and 220° C. In the infrared absorption spectra (by the Nujol Method), they exhibit an absorption by the deformation frequencies of $NH_3^+$ within the range of from 1500 and 1520 $cm^{-1}$ and a wide absorption peak by the vibration frequencies of C=O of $CO_2^-$ within the range of the from 1590 to 1640 $cm^{-1}$. In the mass spectra, their parent peaks are extremely weak and the $[M-CO_2H]^+$ ions appear in conspicuous peaks.

It was confirmed by experiments that the halogenated α-amino acids of the present invention exhibit insecticidal activity, fungicidal activity, herbicidal activity and enzyme-inhibiting activity and serve effectively as insecticidal, fungicidal, herbicidal and enzyme-inhibiting agents.

Insecticidal activity

Cabbage leaves were immersed in a 500-ppm aqueous $CF_2BrCF_2CH_2CH(NH_2)CO_2H$ solution, removed from the solution and dried. They were placed in a Petri dish, in which a group of diamondback moths (Plutella maculipennis Curtis) were fed on the cabbage leaves. After 10 days, 70% of the insects were dead. When the same number of diamondback moths were fed on cabbage leaves which had not been given the treatment, only 10% of the insects were dead after 10 days.

Fungicidal activity

Qualitative observation was conducted by the paper disc method. Specifically, a potato-agar culture medium with which stated microorganic spores had been blended was placed in Petri dishes and paper discs 8 mm in diameter which had been immersed in 500-ppm aqueous solutions of fluorine-containing amino acids, i.e. $CF_2ClCFClCH_2CH(NH_2)CO_2H$ and $CF_2BrCF_2CH_2CH(NH_2)CO_2H$, were spread on top of the aforementioned culture medium. When the culture medium was examined after two days, $CF_2ClCFClCH_2CH(NH_2)CO_2H$ was found to have impeded the growth of the germs of black spot (Alternaria kikuchiana Tanka) and melanose (Diaporthe citri Wolf) and $CF_2BrCF_2CH_2CH(NH_2)CO_2H$ to have impeded the growth of the germs of blast (Pyricularia oryzae Cavara) and bacterial leaf blight (Xanthomonas oryzae Dowson).

Herbicidal activity

Paddy-field soil kneaded in a concrete mixer was placed in 500-ml plastic beakers. Seeds of barnyardgrass (Echinochloa crusgalli Beauv.) were scattered on the soil and incorporated in the soil to a depth of about 2 cm from the surface. Afterward, the seeds of pickerelweed (Monochloria vaginalis var. plantaginea) and purple loosestrife (Lythrum anceps) were scattered on the surface of soil. Then, slender spikerush (Eleocharis acicularis) and rice were transplanted to the soil. The soil in the beakers was inundated to a depth of about 3 cm. After two days, 1% aqueous solution of $CF_2ClCFClCH_2CH(NH_2)CO_2H$ and $CF_2BrCF_2CH_2CH(NH_2)CO_2H$ were applied to the soil in the beakers at dosage rates of 1000 g, 500 g, and 250 g per 10 acres with the aid of a pipet. After 15 days, the miniature paddy fields were examined. Consequently, $CF_2ClCFClCH_2CH(NH_2)CO_2H$ was found to have completely destroyed pickerelweed and purple loosestrife at all the dosage rates tested. $CF_2BrCF_2CH_2CH(NH_2)CO_2H$ was found to have completely destroyed the weeds at the dosage rate of 1000 g/10 acres and half destroyed them at the lower dosage rates of 500 g and 250 g/10 acres.

Enzyme inhibiting activity

A $2 \times 10^{-4}$ M aqueous solution of fluorine-containing amino acid was prepared by adding a fluorine-containing amino acid, viz. $CF_2ClCHFCH_2CH(NH_2)CO_2H$, dissolved in a small amount of methanol to a mixture consisting of 0.1 cc of a 0.025% aqueous solution of acid phosphatase, 0.1 mol of a substrate, 0.05 cc of DPNP, 0.25 cc of water and a 0.1 N sodium acetate (pH 5) as a buffer. The resultant mixture was incubated at 37° C. for 20 minutes. At the end of the 20 minutes, the reaction proceeding in the mixture was stopped by adding 3 cc of an aqueous NaOH solution to the mixture. The mixture was assayed for absorption at a wavelength of 422 mμ. An enzyme inhibition of 58% was found.

When the procedure was repeated by using a $1 \times 10^{-3}$ M aqueous solution of $CF_2ClCFClCH(CH_3)CH(NH_2)CO_2H$, the enzyme inhibition ratio was 37%.

Now, the component reactions which constitute the procedure for the preparation of the compounds of this invention will be described.

The addition reaction of a halogenated ethane and an ester of acrylic acid or crotonic acid under the radiation of light is carried out in the absence of a solvent or in the presence of an inactive solvent such as 1,1,2-trichlorotrifluoroethane at room temperature. The radiation of light is effected by use of an external or internal radiation type high-voltage mercury vapor lamp (with wavelengths preponderantly within the range of from 3650 to 3663 Å) for a period of 10 to 50 hours. Generally, the conversion improves with increasing duration of the radiation of light.

The proportion of the acrylic ester or crotonic ester to the halogenated ethane is 0.5 to 2 mols of the ester per mol of the halogenated ethane. When the addition reaction is carried out in the presence of an inactive solvent, the ratio by weight of the solvent to the reactants is desired to fall within the range of from 1:10 to 10:1. The reaction of the resultant adduct with sodium azide is carried out in ethanol as the solvent containing no water or containing up to 30% of water under reflux at an elevated temperature. In the case of an adduct resulting from use of a crotonate, this reaction requires application of heat for a longer time. The proportion of the sodium azide to the adduct in this reaction is desired to be 1.5 to 2.0 mols of the sodium azide to each mol of the adduct. When the proportion falls outside this range, the yield is lowered and the isolation of the reaction product from the mixture becomes complicated. When this reaction is carried out in a solvent, the proportion of the solvent to the sodium azide is desired to be 20 to 40 parts per part of the sodium azide by weight.

The reduction of the resultant α-azide ester with hydrogen is carried out in an alcohol such as methanol or ethanol as the solvent in the presence of a palladium or platinum catalyst at room temperature.

Specifically, the reduction is performed by dissolving the α-azide ester in the solvent, suspending the catalyst in the solution and, with the resultant mixture kept stirred, causing hydrogen gas to pass through the mixture in small bubbles at a flow rate within the range of from 10 to 20 ml/min for 20 to 30 hours. The solvent is used in an amount 2 to 10 times the amount of the α-azide ester by weight ratio. The amount of the catalyst added to the reaction system is desired to fall in the range of from 0.5 to 2% by weight based on the α-azide ester. When the amount of the catalyst is less than the lower limit of this range, the reaction must be continued for an excessively long time. When some part of the α-azide ester remains unaltered, the isolation of the product after the reaction becomes complicated. The products of the component reactions can be isolated by vacuum distillation. The hydrolysis of the α-amino ester is performed in the presence of sulfuric acid or hydrochloric acid under reflux at an elevated temperature for one to two hours. Then by neutralizing the resultant hydrolyzate by addition of aqua ammonia and expelling water by distillation, the α-amino acid aimed at is obtained in the form of a white solid.

Now, the present invention will be described more specifically with reference to working Examples below.

EXAMPLE 1

In a transparent quartz tube having an inner volume of 300 ml, 48 g (0.20 mol) of 1-chloro-2-iodo-1,1,2-trifluoroethane and 26 g (0.24 mol) of ethyl acrylate were placed in conjunction with 100 ml of 1,1,2-trichlorotrifluoroethane and were exposed to an ulraviolet ray issuing from a spiral light source for 25 hours. After this irradiation, the solvent trichlorotrifluoroethane was expelled from the resultant mixture by distillation under normal pressure and, subsequently, the unaltered reactants were recovered by distillation under a slightly lowered pressure. By subjecting the remaining reaction mixture to vacuum distillation, there was obtained 9.5 g (0.028 mol) of ethyl 2-iodo-4,5,5-trifluoro-5-chloropentanoate of b.p. 79° to 82° C./3 mm, $n_D^{20}$ 1.4610, $d_4^{20}$ 1.728 and $\nu_{C=O}$ 1732 cm$^{-1}$. This adduct was a mixture of two diastereomers (42:58). This reaction by-produced ethyl 4,5,5-trifluoro-5-chloro-2-pentanoate due to removal of hydrogen iodide from the adduct and ethyl 4,5,5-trifluoro-5-chloropentanoate due to substitution of iodine with hydrogen, etc. in small amounts.

In 40 ml of 80% ethanol, 5.7 g (0.016 mol) of the aforementioned ethyl-2-iodo-4,5,5-trifluoro-5-chloropentanoate and 1.94 g (0.030 mol) of sodium azide were stirred under reflux at an elevated temperature for one hour. Water was added to the resultant mixture and ethyl 2-azido-4,5,5-trifluoro-5-chloropentanoate was extracted with ether, then dried and freed from ether by distillation. By vacuum distilling the remaining liquid, there was obtained 3.53 g (0.014 mol, yield of 82%) of ethyl 2-azido-4,5,5-trifluoro-5-chloropentanoate having b.p. 70°–71° C./3 mm, $n_D^{20}$ 1.4221, $d_4^{20}$ 1.333, $\nu_{N_3}$ 2120 cm$^{-1}$ and $\nu_{C=O}$ 1749 cm$^{-1}$.

Thereafter, 4.76 g (0.018 mol) of ethyl 2-azido-4,5,5-trifluoro-5-chloropentanoate was dissolved in 20 ml of ethanol. The resultant solution was placed in a three-neck round-bottom flask and 0.50 g of 5% palladium-containing activated carbon was added to the solution, and hydrogen was passed through the resultant mixture at a flow rate of 20 ml/min at room temperature for 22 hours. The catalyst was separated by filtration and the ethanol was expelled by distillation. By vacuum distilling the residual liquid, there was obtained 293 g (0.013 mol, yield of 69%) of ethyl 2-amino-4,5,5-trifluoro-5-chloropentanoate having b.p. 69° to 70° C./3 mm, $n_D^{20}$ 1.4102, $\nu_{NH_2}$ 3386 and 3318 cm$^{-1}$ and $\nu_{C=O}$ 1733 cm$^{-1}$.

For two hours at an elevated temperature, 2.43 g (0.010 mol) of ethyl 2-amino-4,5,5-trifluoro-5-chloropentanoate and 8 ml of 25% sulfuric acid were refluxed. The resultant mixture was cooled and then neutralized with aqua ammonia to pH 7. The white solid which was precipitated (1.11 g) was separated by filtration and the filtrate was concentrated to produce a white solid (0.78 g). Thus was obtained 1.89 g (0.09 mol, yield of 89%) of an α-amino acid, 2-amino-4,5,5-trifluoro-5-chloropentanoic acid in the form of white plate-shaped crystals having m.p. 184° to 186° C. (decomposition) and $\nu_{C=O}$ 1584 cm$^{-1}$.

EXAMPLE 2

In a reactor having an inner volume of 500 ml, 81 g (0.29 mol) of 1,2-dichloro-2-iodotrifluoroethane and 76 g (0.66 mol) of ethyl crotonate were placed in conjunction with 200 ml of trichlorotrifluoroethane as the solvent and were exposed to an ulraviolet ray from an inner radiation type reaction system for 25 hours. By distilling the resultant solution there was obtained 6.93 g (0.017 mol) of ethyl 2-iodio-3-methyl-4,5-dichloro-4,5,5-trifluoropentanoate having b.p. 88° to 89° C./3 mm, $n_d^{20}$ 1.4786, $d_4^{20}$ 1.744 and $\nu_{C=O}$ 1739 cm$^{-1}$.

Besides, the reaction gave 1.92 g (0.0049 mol) of ethyl 2-(1-iodoethyl)-3,4-dichloro-3,4,4-trifluorobutanoate as a main by-product.

Then in 350 ml of 80% ethanol, 31 g (0.0080 mol) of ethyl 2-iodo-3-methyl-4,5-dichloro-4,5,5-trifluoropentanoate and 26 g (0.040 mol) of sodium azide were refluxed at an elevated temperature for 22 hours. By treating the product by following the procedure of Example 1, there was obtained 3.03 g (0.0098 mol, yield of 12%) of ethyl 2-azido-3-methyl-4,5-dichloro-4,5,5-trifluoropentanoate having b.p. 94° C./4 mm, $n_D^{20}$ 1.4420, $\nu_{N_3}$ 2113 cm$^{-1}$ and $\nu_{C=O}$ 1748 cm$^{-1}$.

In this case, this reaction simultaneously produced 10.7 g (0.040 mol, yield of 51%) of 3-methyl-4,5-dichloro-4,5,5-trifluoro-2-pentanoate having b.p. 82° to 86° C./7 mm, $n_D^{20}$ 1.4330, $d_4^{20}$ 1.344 and $\nu_{C=O}$ 1734 cm$^{-1}$, $\nu_{C=C}$ 1657 cm$^{-1}$.

In 30 ml of ethanol, 2.14 g (0.0070 mol) of ethyl 2-azido-3-methyl-4,5-dichloro-4,5,5-trifluoropentanoate and 0.61 g of 5% palladium-containing activated carbon were placed and bubbled with hydrogen gas (at a flow rate of 15 ml/min) for 22 hours. Consequently there was obtained 1.04 g (0.0037 mol, yield of 53% of ethyl 2-amino-3-methyl-4,5-dichloro-4,5,5-trifluoropentanoate having b.p. 71° C./2 mm, $n_D^{20}$ 1.4328, $\nu_{NH_2}$ 3398 and 3327 cm$^{-1}$ and $\nu_{C=O}$ 1740 cm$^{-1}$.

By hydrolyzing 0.81 g (0.0029 mol) of the aforementioned ethyl 2-amino-3-methyl-4,5-dichloro-5,5,5-trifluoropentanoate by the procedure of Example 1, there was produced 0.59 (0.0023 mol, yield of 80%) of 2-amino-3-methyl-4,5-dichloro-4,5,5-trifluoropentanoic acid in the form of white plate-shaped crystals having m.p. 179° to 181° C. (decomposition) and $\nu_{C=O}$ 1640 cm$^{-1}$.

EXAMPLE 3

In a transparent quartz tube having an inner volume of 300 ml, 61 g (0.20 mol) of 1-bromo-2-iodo-tetrafluoroethane and 24 g (0.24 mol) of ethyl acrylate were placed in conjunction with 105 ml of 1,1,2-trichlorotrifluoroethane and were exposed to an ultraviolet ray from a spiral type light source for 25 hours. After expulsion of the solvent trichlorotrifluoroethane and the unaltered portions of the reactants by distillation, the residual mixture was subjected to vacuum distillation to afford 32 g (0.079 mol) of ethyl 2-iodo-4,4,5,5-tetrafluoro-5-bromopentanoate having b.p. 104° to 15° C./11 mm, $n_D^{20}$ 1.4641, $d_4^{20}$ 1.954 and $\nu_{C=O}$ 1740 cm$^{-1}$. The reaction by-produced ethyl-4,4,5,5-tetrafluoro-5-bromo-2-pentenoate due to removal of hydrogen oxide from the adduct and ethyl 4,4,5,5-tetrafluoro-5-bromopentanoate due to substitution of iodine with hydrogen, etc. in small amounts.

Subsequently, 9.7 g (0.024 mol) of ethyl 2-iodo-4,4,5,5-tetrafluoro-5-bromopentanoate and 2.73 g (0.042 mol) of sodium azide were added to 40 ml of 80% ethanol and were refluxed while under stirring at an elevated temperature for one hour. Then water was added to the resultant mixture and 2-azido-4,4,5,5-tetrafluoro-5-bromopentanoate was extracted with ether, whereafter the ether was removed by drying. The residual liquid was vacuum distilled to afford 4.54 g (0.014 mol, yield of 60%) of ethyl 2-azido-4,4,5,5-tetrafluoro-5-bromopentanoate having b.p. 78° to 79° C./4 mm, $n_D^{20}$ 1.4291, $d_4^{20}$ 1.564, $\nu_{N_3}$ 2120 cm$^{-1}$ and $\nu_{C=O}$ 1746 cm$^{-1}$.

Subsequently, 6.36 g (0.020 mol) of ethyl 2-azido-4,4,5,5-tetrafluoro-5-bromopentanoate was dissolved in 20 ml of ethanol and, with 0.51 g of 5% palladium-containing activated carbon added thereto, hydrogen was caused to pass through the resultant solution at a flow rate of 20 ml/min. at room temperature for 26 hours. The catalyst was separated by filtration and the ethanol was expelled by distillation. By vaccum distilling the residual liquid there was obtained 4.00 g (0.014 mol, yield of 68%) of ethyl 2-amino-4,4,5,5-tetrachloro-5-bromopentanoate having b.p. 72° to 73° C./4 mm, $\nu_{NH_2}$ 3387 and 3309 cm$^{-1}$ and $\nu_{C=O}$ 1738 cm$^{-1}$.

By hydrolyzing 2.05 g (0.007 mol) of the aforementioned ethyl 2-amino-4,4,5,5-tetrafluoro-5-bromopentanoate by the procedure of Example 1, there was obtained 1.61 g (0.006 mol, yield of 87%) of 2-amino-4,4,5,5-tetrafluoro-5-bromopentanoic acid in the form of white plate shaped crystals having m.p. 216° to 218° C. (decomposition) and $\nu_{C=O}$ of 1593 cm$^{-1}$.

What is claimed is:

1. A halogenated α-amino acid represented by the general formula:

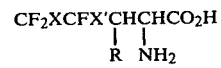

wherein, X is one member selected from the group consisting of Cl and Br, X' is one member selected from the group consisting of F, Cl and H, and R is one member selected from the group consisting of H and CH$_3$.

* * * * *